United States Patent [19]

Manning

[11] 4,259,665
[45] Mar. 31, 1981

[54] DRIVER SLEEP OR FATIGUE ALARM

[75] Inventor: John Manning, Santa Clara, Calif.

[73] Assignee: RMR Systems, Inc., Santa Clara, Calif.

[21] Appl. No.: 42,853

[22] Filed: May 29, 1979

[51] Int. Cl.³ .............................................. G08B 21/00
[52] U.S. Cl. .................................. 340/575; 340/52 D
[58] Field of Search ................ 340/52 D, 53, 573, 575

[56] References Cited

U.S. PATENT DOCUMENTS 3,026,503  3/1962  Scheer .................................. 340/575

Primary Examiner—Alvin H. Waring
Attorney, Agent, or Firm—Hopgood, Calimfade, Kalil, Blaustein & Lieberman

[57] ABSTRACT

An alarm which is actuated when the driver of a vehicle falls asleep or dozes includes spaced conductors affixed to the steering wheel of the vehicle. When the driver is awake, both of the conductors are firmly contacted by one of the driver's hands and a minute current flows between the conductors through the driver's hand. This current maintains a switch in one state in which an alarm is deactuated. Should the driver fall asleep while driving, his hands will lose their grip on the steering wheel and thereby open the conducting path between the conductors. When this occurs, the switch is placed in a second condition in which the alarm becomes actuated to awaken the driver. The alarm may either be mounted to the steering wheel itself or on a cover attached to the wheel.

5 Claims, 4 Drawing Figures

DRIVER SLEEP OR FATIGUE ALARM

This invention relates generally to alarms, and more particularly to an alarm for alerting or awakening an operator of a vehicle should the operator become sleepy while operating the vehicle. Accidents involving automobiles and trucks caused by the driver of the vehicle falling asleep or dozing at the wheel are all too common and cause a large number of vehicular deaths and serious injuries each year.

Devices have been proposed to awaken a driver who dozes off while operating a vehicle, but because of their complexity and cost, these devices have been less than completely satisfactory and few, if any, have been used to the extent desirable to significantly reduce the number of vehicular deaths caused by sleeping or dozing drivers. Moreover, most devices of this nature could only be installed in the automobile at the initial production stage and could not be installed as an aftermarket accessory to the vehicles, which further limits their utility and acceptance.

Accordingly, it is an object of this invention to provide an improved driver sleep alarm.

It is a further object of this invention to provide an improved driver alarm, which may either be assembled in the electrical system of a vehicle during manufacture, or be installed in an automobile as an aftermarket accessory.

It is another object of the present invention to provide a driver alarm of the type described, which is both reliable and free from complexity.

Generally speaking, the driver sleep alarm according to the invention includes a pair of spaced conductors mounted on opposed sides of the rim of the steering wheel which, when the driver is alert, are firmly gripped and contacted by one hand of the driver. In this condition, a trickle of current flows from one conductor to the other through the driver's hand and keeps an alarm circuit deactivated. Should the driver's hand be removed from firm contact with the conductors, as when the driver is beginning to doze or fall asleep, the current path between the conductors will be opened and the alarm will be activated to waken the driver.

Other objects of this invention will become apparent on a reading of the detailed following specification when considered with the attached drawing, in which.

Figure 1:
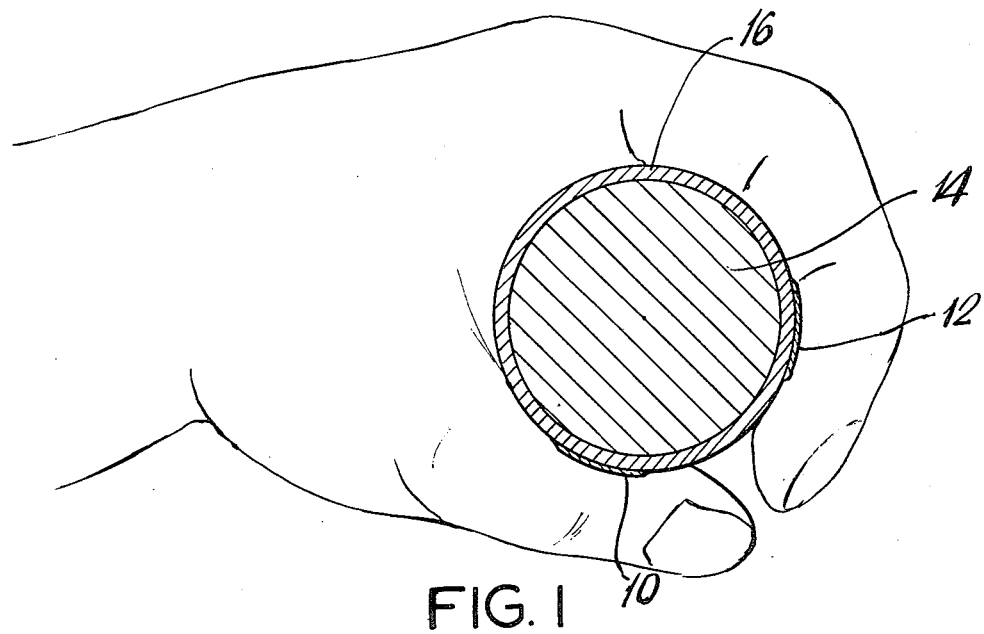
FIG. 1 is a sectional view of a steering wheel having conductors attached thereto and showing a driver's hand contacting the conductors in accordance with the present invention.

The alarm of the invention is activated to awaken a driver whose hands, when the driver begins to doze, lose their firm grip on the vehicle's steering wheel. As shown in FIG. 1, in the alarm of the invention a pair of spaced electrical conductors 10 and 12 are attached to a portion of the periphery of the steering wheel 14. When one hand 16 of the driver is normally gripping the steering wheel in the operation of the vehicle, that hand comes into firm contact with both of the conductors. In the embodiment shown in FIG. 1, conductors 10 and 12 are located on opposite sides of the steering wheel 16 at positions slightly beneath the center line of the wheel so that they will be contacted during normal operation of the vehicle. If the driver becomes sleepy or fatigued, one or both of the conductors will not be tightly contacted by the driver's hand.

The conductors 10 and 12 are connected in an alarm circuit as shown schematically in FIG. 2. As therein shown, conductor 10 is connected to a voltage source V1, through a resistor R, and conductor 12 is connected to ground. One end of resistor R is connected to the set terminal of a flip-flop 18. The output of the flip-flop is applied to a control input terminal of an oscillator 20, which also receives operating current from a voltage source V2 connected to the oscillator through a switch 22, which is operated by the driver to energize the alarm circuit. The output of the oscillator is connected to a transducer, such as a loudspeaker 24.

Figure 2A:
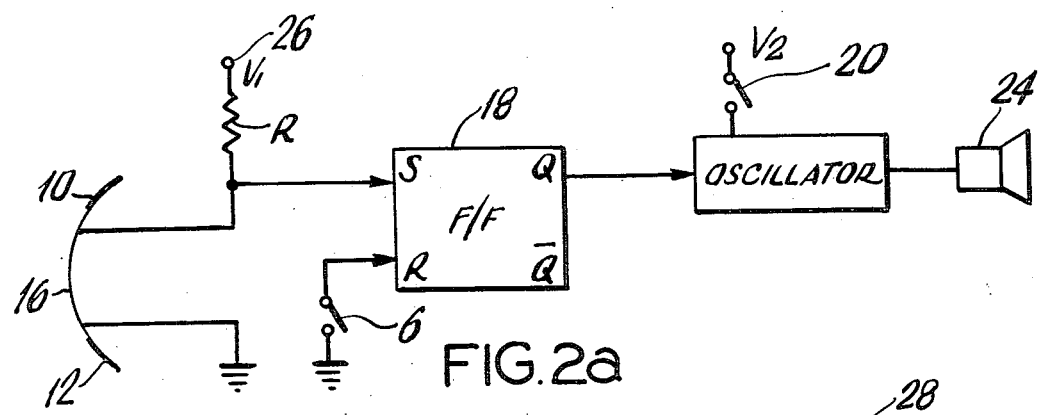
FIG. 2A is a schematic diagram of the circuit of the alarm of the invention.

In the operation of the embodiment of FIGS. 1 and 2A, the driver at a time when he is concerned that he may begin to doze while driving, and preferably at the onset of a trip, energizes the oscillator 20 by closing switch 22. When the driver is alert, as noted, his hand firmly contacts the conductors 10 and 12 on the steering wheel so as to create path shown at 16 in FIG. 2A between the conductors 10 and 12, whereby a trickle of current flows through the driver's hand 16 between the conductors. The amount of current is so minute as to be undetectable by the driver. This trickle of current flowing through resistor R establishes a voltage at the set input of flip-flop 18, which keeps the flip-flop in one state so that oscillator 20 is maintained in the unactivated condition. When the driver's hand 16 loses the firm contact with conductors 10 and 12, the trickle of current flow between the conductors will be interrupted, thus reducing the voltage at the set terminal of flip-flop 18, such that the flip-flop will change its state. As a result, the oscillator 20 will become actuated and an alarm will be produced by transducer 24 to awaken or startle the driver out of his sleepy state. Once the driver is awakened by the alarm, the alarm can be shut off by resetting the flip-flop by the operation of the switch 26 connected between the reset terminal of flip-flop 18 and ground.

Figure 2B:
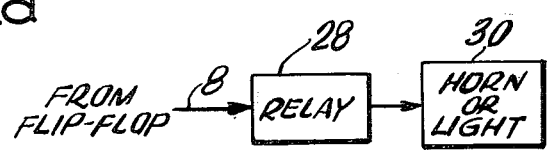
FIG. 2B illustrates a possible modification of the circuit of FIG. 2A.

If desired, and as shown, in FIG. 2B the flip-flop 20 may be connected to operate a relay 28, which, when energized in this manner, activates a horn or light 30, which further aids in alerting or waking the dozing driver.

Figure 3:
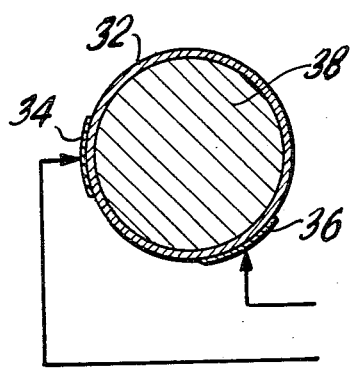
FIG. 3 is a sectional view of another embodiment of the invention in which the conductors are attached to a wheel covering.
Figure 4:
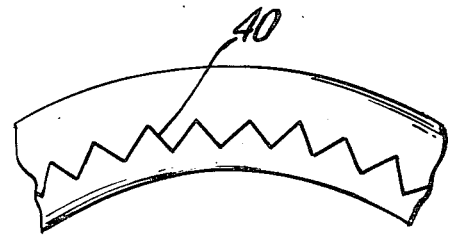
FIG. 4 is an elevation of the wheel cover showing one of the conductors of the embodiment of FIG. 3.

The conductors need not be part of the steering wheel itself, but may be part of a steering wheel cover 32 placed over the wheel. Thus, as shown in FIG. 3, conductors 34 and 36 are disposed on cover 32, in a manner such that when cover 32 is in place about steering wheel 38, conductors 34 and 36 will function in a manner similar to conductors 10 and 12 in the previously described embodiment. Conductors 34 and 36 are, as shown, preferably arranged in a zig-zag pattern 40 arranged on either side of steering wheel 38. The steering wheel cover mounted device is particularly suitable for later installation in a vehicle that is not originally equipped with such a device. The circuitry shown in FIG. 2A may be mounted as a unit to the steering column of the vehicle.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and the appended claims.

What is claimed is:

1. A sleep alarm for use in a vehicle, said alarm comprising first and second spaced conductive means adapted to be arranged on the steering wheel of the vehicle, and arranged as to be contacted by the hand of the driver, means for supplying a trickle of current through said first and second conductive means whenever the driver's hand firmly grips the steering wheel and said first and second conductive means, a solid state flip-flop circuit with its set terminal connected to one of said conductive means and placed in a first state when the driver's hand is firmly gripping the steering wheel and in a second state when the driver's hand loses its firm grip on the steering wheel, and alarm means connected to said solid state flip-flop circuit and being activated when said solid state flip-flop circuit is placed in said second state when the driver's hand loses it firm contact with said conductive means.

2. The alarm device as claimed in claim 1, wherein said first and second conductive means are disposed on opposed sides of the steering wheel.

3. The alarm device as claimed in claim 1, further comprising reset switch means connected to the reset terminal of said flip-flop for turning off said alarm means following the actuation thereof.

4. The alarm device as claimed in claim 1, wherein said first and second conductive means are disposed on a steering wheel cover mounted to said steering wheel.

5. The alarm device as claimed in claim 1, in which said alarm means comprises an oscillator, and further comprising manually operated control means for selectively energizing said oscillator for potential actuation by said switch means.

* * * * *